United States Patent [19]

Soll

[11] Patent Number: 5,722,762
[45] Date of Patent: Mar. 3, 1998

[54] ILLUMINATION DEVICE FOR MOUNTING ON THE HEAD OF A USER

[76] Inventor: David B. Soll, 5001 Frankford Ave., Philadelphia, Pa. 19124

[21] Appl. No.: 683,281

[22] Filed: Jul. 18, 1996

[51] Int. Cl.⁶ .................................................. F21L 15/14
[52] U.S. Cl. ........................... 362/105; 362/184; 362/187
[58] Field of Search ............................ 351/158; 362/105, 362/184, 187, 190, 191, 238, 239

[56] References Cited

U.S. PATENT DOCUMENTS

| | | | |
|---|---|---|---|
| 1,688,113 | 10/1928 | Bornkessel | 362/105 |
| 1,705,465 | 3/1929 | Cameron | 362/105 |
| 1,741,264 | 12/1929 | Wappler | 362/105 |
| 2,289,488 | 7/1942 | Dritsas | 362/105 |
| 2,638,532 | 5/1953 | Brady | 362/105 |
| 2,659,824 | 11/1953 | Burnham | 33/286 |
| 2,904,670 | 9/1959 | Calmes | 362/105 |
| 3,014,405 | 12/1961 | Swikart | 362/105 |
| 3,060,308 | 10/1962 | Fortuna | 362/105 |
| 3,087,049 | 4/1963 | Schecter | 362/105 |
| 3,350,552 | 10/1967 | Lawrence | 362/105 |
| 3,634,676 | 1/1972 | Castellano | 362/105 |
| 3,683,168 | 8/1972 | Tatje | 362/105 |
| 3,769,663 | 11/1973 | Perl | 362/105 |
| 4,616,297 | 10/1986 | Liu | 362/105 |
| 4,794,496 | 12/1988 | Lanes et al. | 362/105 |
| 4,920,466 | 4/1990 | Liu | 362/105 |
| 4,959,760 | 9/1990 | Wu | 362/105 |
| 4,967,323 | 10/1990 | Johnson et al. | 362/103 |
| 5,230,558 | 7/1993 | Jong | 362/105 |

FOREIGN PATENT DOCUMENTS 20821  12/1907  United Kingdom .................. 362/105

*Primary Examiner*—Alan Cariaso
*Attorney, Agent, or Firm*—Panitch Schwarze Jacobs & Nadel, P.C.

[57] ABSTRACT

An illumination device for mounting on the head of a user including a frame having a cross member and a pair of rearwardly extending temple members attached to opposite ends of the cross member. At least one focusable light assembly is rotatably mounted to the frame and includes a light source for emitting light. The light assembly is adjustable by the user for varying the vergence and direction of the light emitted from the light source.

10 Claims, 2 Drawing Sheets

ILLUMINATION DEVICE FOR MOUNTING ON THE HEAD OF A USER

FIELD OF THE INVENTION

The present invention relates to an illumination device and, more particularly, to a focusable illumination device incorporated into a specialized eyeglass-type frame which includes at least one focusable light assembly.

BACKGROUND OF THE INVENTION

Illumination devices designed to be worn on the head of a person or user are generally known. Several variations of such devices, sometimes referred to as illuminating spectacles, have been developed for activities occurring in dark or poorly lighted areas. For example, head-mounted illumination devices have been known for use by electricians working in basements, attics, or closets, for meter readers when in dark environments, such as basements, and for night delivery people. Such prior art devices are advantageous over the use of an ordinary hand-held flashlight in that the devices leave both of the user's hands free to perform work.

Known head-mounted illumination devices range from simple clip arrangements for clipping flashlights onto eyeglasses to illumination devices that also provide the user with a temple massage. Generally, the light sources of the known devices, hereinafter referred to as lamps, are rigidly mounted to an eyeglass frame so that there is no relative movement between the frame and the lamp. Without relative movement, such devices require the user to orient his or her head in a given direction to direct light beams emitted from the lamp to a particular object.

In other known devices, the user has some ability to direct the light beams without movement of his or her head. However, the range of movement of the lamps is fairly limited. Several head-mounted illumination devices have only a single lamp placed on a frame, usually positioned at the center of the users's forehead, which can be rotated in a single plane; i.e., up/down or side to side. Other devices have two lamps, placed either above or outside of each eye. Generally, the devices with two lamps are designed so that the emitted light beams are directed toward each other and overlap at a fixed distance from the user.

While the known prior art devices are suitable for some applications where "hands free" illumination is required, the user has no ability to control the intensity of the illumination incident upon a viewed object except to change the distance between the viewed object and the illumination device, and thus his or her head and the object. In other words, the user must move closer to the object to decrease the area of the illumination upon the object, thereby increasing the intensity of the illumination. In addition to the inconvenience of this adjustment method, the extent by which the intensity of illumination can be practically adjusted is very limited. The known prior art illumination devices generally are provided with either a frame-mounted battery or a remote connected power source. The prior art illumination devices do not have the capability of utilizing both a remote power source for certain applications and a frame-mounted battery when electrical connection to a remote source would be inconvenient. The known devices are also limited in their ability to direct the beams of light from the lamps independently of adjusting the position of the user's head relative to the object to be illuminated.

Because of the limitations in the known "hands free" illumination devices, these devices provide little or no assistance to persons with macular degeneration. Macular degeneration is a condition in which the afflicted, while retaining the ability to use peripheral vision or vision limited areas of their view normal field, have limited ability to see detail due to poor retinal function in the center or other portions of the retina. The retina is the structure in the inside of the eye which receives light reflected from viewed objects and transmits the light as images to the brain. The macula is the central or "reading" portion of the retina, and if it is not functioning properly, a clear image cannot be correctly received and interpreted by the brain. Frequently, a significant increase in the amount of light incident upon an object in a functioning area of a person field of view can substantially improve the details of the image seen of that object by a person afflicted with macular degeneration or other eye conditions and allow the patient to interpret the image, for example to be able to read text.

The present invention is a result of observation of the lack of illumination devices which could be used by persons with macular degeneration to improve their ability to see. Accordingly, the illumination device of the present invention has the potential to improve the ability of persons with macular degeneration or other eye disorders to see more clearly.

SUMMARY OF THE INVENTION

Briefly stated, the present invention relates to an illumination device for mounting on the head of a user. The illumination device includes a frame having a cross member and a pair of rearwardly extending temple members attached to opposite ends of the cross member. At least one focusable light assembly is rotatably mounted to the frame and includes a light source for emitting light. The light assembly is adjustable by the user for varying the vergence of light emitted from the light source and the direction of the source of the light.

BRIEF DESCRIPTION OF THE DRAWINGS

The foregoing summary, as well as the following detailed description of preferred embodiments of the invention, will be better understood when read in conjunction with the appended drawings. For the purpose of illustrating the invention, there are shown in the drawings embodiments which are presently preferred. It should be understood, however, that the invention is not limited to the precise arrangements, configurations and instrumentalities shown. In the drawings.

DETAILED DESCRIPTION OF THE PREFERRED EMBODIMENTS

Figure 1:
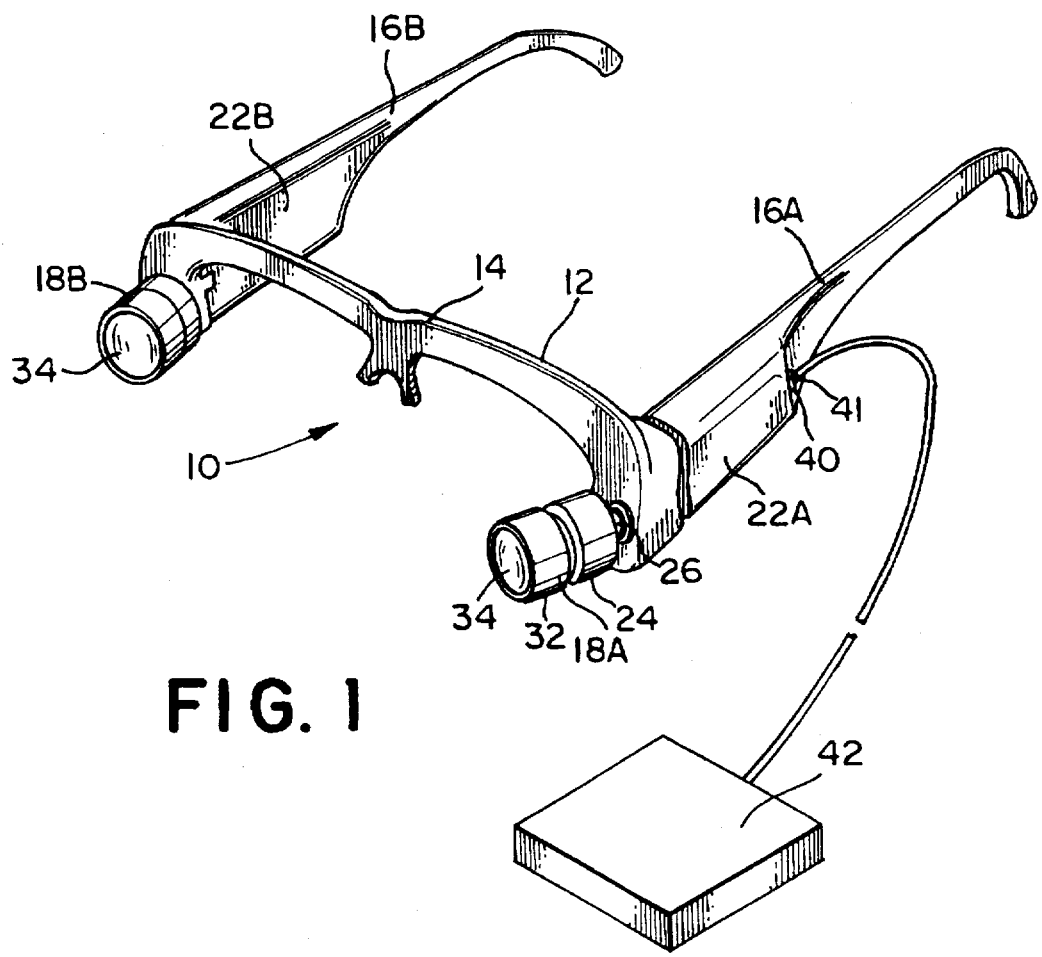
FIG. 1 is a perspective view of an illumination device in accordance with a first preferred embodiment of the present invention.

Certain terminology is used in the following description for convenience only and is not limiting. The words "right,"

"left," "lower" and "upper" designate directions in the drawings to which reference is made. The words "inwardly" and "outwardly" refer to directions toward and away from, respectively, the geometric center of the illumination device and designated parts thereof. The terminology includes the words above specifically mentioned, derivatives thereof and words of similar import.

Figure 2:
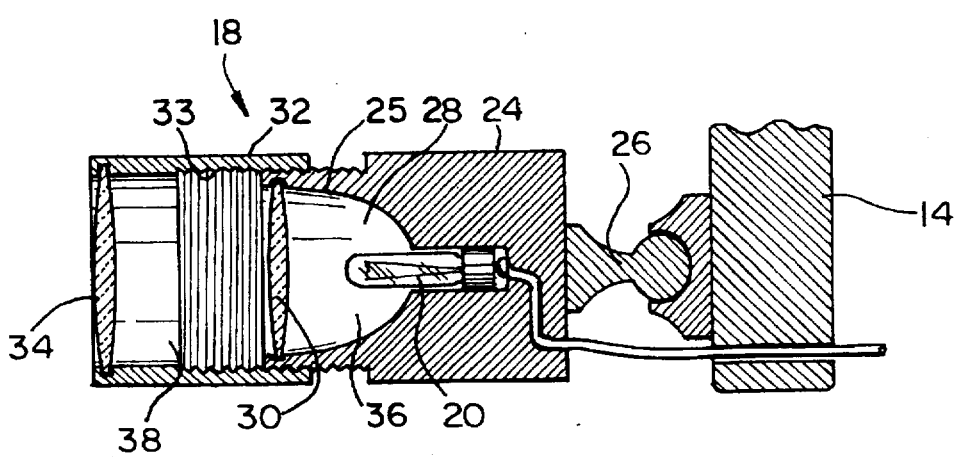
FIG. 2 is an enlarged cross-sectional view of a focusable light assembly of the type shown in FIG. 1.

Referring now to the drawings in detail, wherein like numerals indicate like elements throughout, there is shown in FIGS. 1 and 2 an illumination device, generally designated 10, in accordance with a first preferred embodiment of the present invention for mounting on the head of a person or user. The illumination device 10 includes a frame 12, generally shaped like a pair of lensless glasses, having a cross member 14 and a pair of rearwardly extending temple members 16A, 16B attached to opposite ends of the cross member 14. Preferably, the temple members 16A, 16B are connected to the cross member 14 with hinges in a manner generally known to those of ordinary skill in the art, to allow the frame 10 to be folded to a compact size when not in use.

Still with reference to FIG. 1, at least one but preferably two battery compartments 22A, 22B are attached to or made part of the frame 12, the purpose of which is explained in detail below. Preferably, each battery compartment 22A, 22B is mounted to or integral with a respective temple member 16A, 16B, and is sized to accommodate one or more batteries (not shown) of a standard or special size. However, it will be understood by the skilled artisan from the present disclosure that the battery compartments 22A, 22B could be located on or integral with the cross member 14, and that a single battery compartment or more than two battery compartments could be utilized, if desired.

In the present embodiment, the cross member 14 and the temple members 16A, 16B are preferably constructed of a metal alloy, such as aluminum or stainless steel, in a manner generally known to those skilled in the art. However, other materials such as titanium, steel or a suitable polymeric material could be used for the cross member 14 and/or the temple members 16A, 16B. The battery compartments 22A, 22B may be machined or molded with the temple members 16A, 16B. However, it is within the scope of the present invention to construct the temple members 16A, 16B and the battery compartments 22A, 22B of some other suitable material and/or to construct the components separately and join the components together in a subsequent assembly operation.

Referring now to FIGS. 1 and 2, at least one and preferably more focusable light assemblies 18A, 18B are rotatably mounted to the frame 12. Preferably two such generally identical focusable light assemblies 18A, 18B are provided with only a single light assembly 18 being described in detail with reference to FIG. 2. As shown in FIG. 2, each focusable light assembly 18 includes a light source 20 for emitting light, the light assembly 18 being adjustable by the user for varying the vergence of light emitted from the light source 20 over a predetermined range.

As shown in FIG. 2, the focusable light assembly 18 includes a base member 24 mounted to the frame 12, which in the preferred embodiment, is attached to the frame 12 by means of a ball and socket joint 26 which can be rotated in any direction to illuminate a selected area. The base member 24 has a cavity 28 and a first, generally fixed lens 30 mounted in and proximate to the open end of the cavity 24. The light source 20 is also disposed within cavity 28 of base member 24 and is preferably a high intensity light source, such as a halogen bulb. However, it is within the scope of the present invention to make light source 20 a standard light bulb, a light emitting diode, or any other appropriate source of light.

A focusing sleeve 32 is movably engaged with the base member 24 proximate the open end of the cavity 28 and has a second lens 34 mounted therein. The focusing sleeve 32 is axially displaceable with respect to base member 24 to permit the user to vary the distance between the first lens 30 and the second inns 34 to converge or diverge the light emitted from light source 20. Preferably, the focusing sleeve 32 includes internal threads 33 and the base member 24 includes external threads 25 such that rotating the focusing sleeve 32 with respect to the base member 24 results in axial displacement of the focusing sleeve 32 relative to the base member 24 to move the second lens 34 toward or away from the first lens 30. This type of arrangement allows relatively fine control of the displacement of the focusing sleeve 32 and accordingly, fine control of the distance between the first and second lenses 30, 34. However, it will be understood by those skilled in the art that the focusing sleeve 32 could be mounted with a sliding fit on the base member 24 and could be moved axially in a telescoping manner or could be mounted for movement relative to the base member 24 in any other manner known to those skilled in the art.

In the preferred embodiment, the illumination device 10 has two focusable light assemblies 18A, 18B mounted to the cross member 14, with each of the light assemblies being disposed proximate to the opposite ends of the cross member 14, as shown in FIG. 1. However, it is understood by those skilled in that art that the light assemblies 18A, 18B could be mounted to the cross member 14 at other locations or that the illumination device 10 could have a single focusable light assembly 18 mounted in the center of the cross member 14 or at any other suitable location on the frame 12.

Preferably, the base member 24 and focusing sleeve 32 are fabricated from a molded polymeric material, or are cast or machined from a metallic materials such as aluminum, steel, stainless steel or titanium. The base member 24 and the focusing sleeve 32 need not be constructed of the same material. The first lens 30 and the second lens 34 are preferably ground and polished glass or a molded clear polymeric material and the type and magnification provided by each lens can be varied in order to achieve the desired field of illumination and intensity ranges for a given application.

The ball and socket joint 26 is preferably constructed of molded polymeric material, and may be formed integrally with the base member 24 and the cross member 14, if desired, or could be attached in a secondary operation by an adhesive connection or a suitable mechanical fastener. However, those skilled in the art will recognize from the present disclosure that the ball and socket joint 26 can be made by various other methods, such as casting or machining, and may be made from a metallic material, or any other suitable material. A friction fit is provided between the ball and socket connection to maintain the focusable light assemblies 18A, 18B in a given position as adjusted by the user to illuminate a selected area. It will be understood by those skilled in the art from the present disclosure that other types of connectors can be utilized to provide a full range of vertical and horizontal motion for aiming the focusable light assemblies 18A, 18B, such as a bendable mount or a double pivot arrangement, if desired. The selection of suitable materials for the elements of the focusable light assembly 18A, 18B can vary depending upon the particular application and is well within the capabilities of one skilled in the art.

In the preferred embodiment, as shown in FIG. 2, the cavity 28 of the base member 24 has a paraboloidal surface 36, and the light source 20 is at least partially disposed within an area surrounded by the paraboloidal surface 36. The light emitted from the light source 20 projects from the widest cross-section of the paraboloidal surface 36. Preferably, the cavity 28 and the inner wall 38 of focusing sleeve 32 are coated or lined with a reflective substance or material for concentrating light emitted from the light source 20. However, those skilled in the art will recognize that the focusable light assembly 18 does not require either the paraboloidal surface 36 or the reflective coating to function as intended.

While in the present embodiment it is preferred that the focusable light assembly 18A, 18B be comprised of the base member 24, the focusing sleeve 32, the first lens 30 and the second lens 34, it is understood by those skilled in the art that focusable light assembly 18 could be constructed with only one lens or with an aperture stop arrangement (not shown) without the need for any lenses. Furthermore, the focusable light assembly 18 could be provided by any other suitable means for changing the vergence of an emitted beam of light, and the present invention is intended to embrace all possible constructions of the focusable light assembly 18 which can permit the user to make suitable adjustments for varying the vergence of light emitted from the light source 20.

Referring to FIG. 1, an electrical connector 40 is attached to or formed within the frame 12 to provide a removable electrical connection between at least one of the light sources 20A, 20B and an external electrical power source 42. The light sources 20A, 20B of the focusable light assemblies 18A, 18B, respectively, are in electrical communication with each other via at least one conductor (not shown). When the electrical connector 40 is in communication with the external power source 42, electrical communication is established between the external power source 42 and both light sources 20A and 20B. In the preferred embodiment, the electrical connector 40 is a standard electrical plug or socket, of the type generally known to those skilled in the art. A mating plug or socket portion 41 is attached to a line extending from the power source 42. Preferably, the external power source 42 is a transformer or a battery pack.

As shown in FIG. 1, two batteries (not shown) are preferably installed in the present embodiment 10, with each battery being disposed within one of the battery compartments 22A and 22B being in electrical communication with one of the light sources 20A, 20B. The batteries provide power to the light sources 20 when the external power source 42 is not available or inconvenient. Preferably, the batteries are rechargeable and electrical circuitry is provided in the battery compartments 22A, 22B which enables the batteries to be re-charged by the power source 42. Such recharging circuits are known to those skilled in the art and, accordingly, further description is not believed necessary or limiting. However, it is within the scope of the present invention to use any other type of battery and to omit the re-charging electrical circuitry in battery compartments 22A, 22B.

In the first preferred embodiment, a user has the option of utilizing either the external power source 42 connected to the electrical connector 40 or one or more batteries located within each of the battery compartments 22A, 22B to provide power for the light sources 20A, 20B. The frame 12 is also adapted to fit over standard eyeglasses to enable the illumination device 10 to be utilized with or without a pair of eyeglasses.

Figure 3:
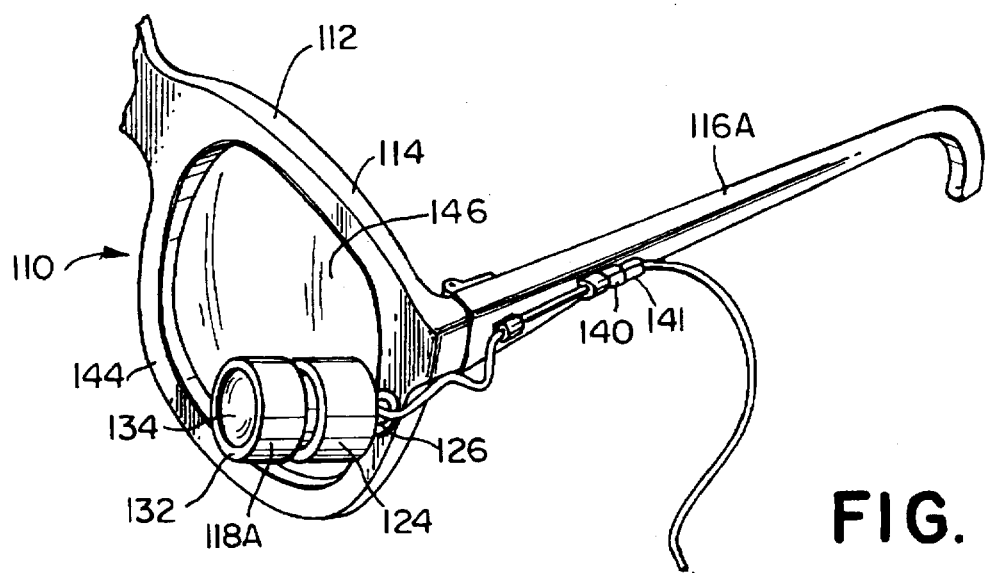
FIG. 3 is a partial perspective view of a second preferred embodiment of the present invention with a second construction of the frame.

Referring now to FIG. 3, there is shown a second preferred embodiment of an illumination device, generally designated 110, for mounting on a user's head, in accordance with the present invention. The second preferred embodiment of the illumination device 110 is similar to the first preferred embodiment of the illumination device 10 described above, and like elements have been designated with the same element numerals but with the addition of 100. The differences from the first embodiment of the illumination device 10 are described in detail below.

The second preferred embodiment of the illumination device 110 includes a frame 112 having a cross member 114 and a pair of rearwardly extending temple members 116A, 116B attached to opposite ends of the cross member 114. The second preferred embodiment of the present invention further includes a pair of lens sockets 144 attached to the cross member 114. Two lenses 146 are provided with one lens 146 being mounted within each of the lens sockets 144. Preferably, lens sockets 144 are fabricated from the same type of material as the cross member 114 and temple members 116A, 116B. The lenses 146 could be any type of corrective lenses or could be planar lenses, such as those used in safety glasses, and can be constructed of glass, optical grade polymeric material, or any other suitable material. The focusable light assemblies 118A, 118B are mounted to the frame 112 and are used in the same manner as in the first embodiment 10, described above.

In the second preferred embodiment, frame 112 does not include battery compartments, and therefore, the user must utilize the external power source 142 by connecting it to the electrical connector 140 mounted on the frame 112. Without batteries and battery compartments, less weight is supported by a user's head when using the second embodiment 110 as compared with using the first embodiment 10 of the invention. Additionally, the focusable light assemblies 118A, 118B may be removably mounted to the frame 112 such that the frames 112 are suitable for normal usage without the focusing light assemblies 118A, 118B attached, if desired.

Figure 4:
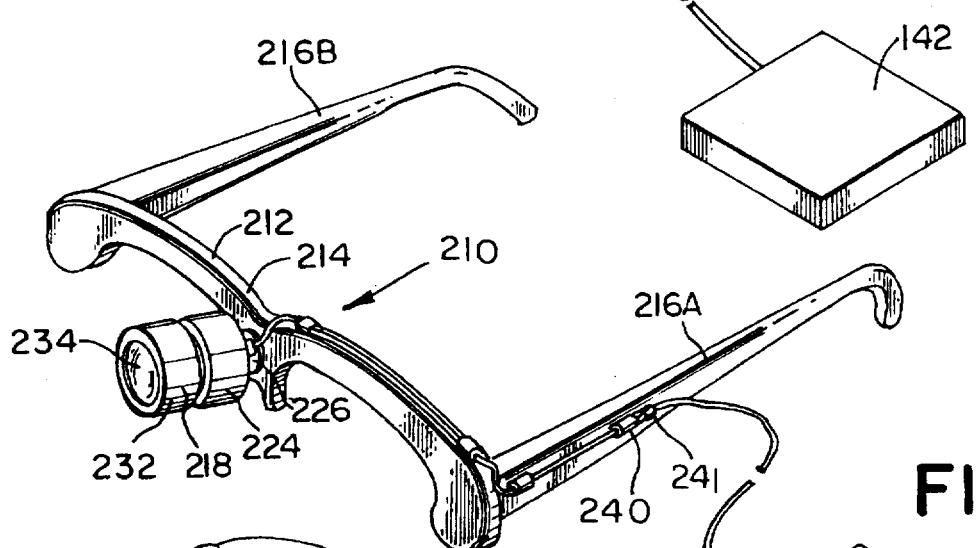
FIG. 4 is a perspective view of a third preferred embodiment of the present invention.

Referring now to FIG. 4, there is shown a third preferred embodiment of an illumination device, generally designated 210, for mounting on a user's head, in accordance with the present invention. The third preferred embodiment of the illumination device 210 is similar to the first preferred embodiment of the illumination device 10 described above, and like elements have been designated with the same element numerals but with the addition of 200. The differences from the first embodiment of the illumination device 10 are described in detail below.

The third preferred embodiment of the illumination device 210 includes a frame 212 having a cross member 214 and a pair of rearwardly extending temple members 216A, 216B attached to opposite ends of the cross member 214. One focusable light assembly 218 is mounted to the frame 212 in the same manner as in the first embodiment 10 described above and is preferably disposed near the center of the cross member 214. Focusable light assembly 218 is used in the same manner as in the first embodiment 10, described above.

In the third preferred embodiment, frame 212 does not include battery compartments, and therefore, the user must utilize the external power source 242 by connecting it to the electrical connector 240 mounted on the frame 212. As with the second preferred embodiment, without batteries and battery compartments, less weight is supported by a user's head when using the third embodiment 210 as compared with using the first embodiment 10 of the invention. However, it will be appreciated by those skilled in the art that the third preferred embodiment 210 could be constructed to include one or more battery compartments so as to provide the user with the option of utilizing either the power source 242 or batteries to supply power to light source 220.

Figure 5:
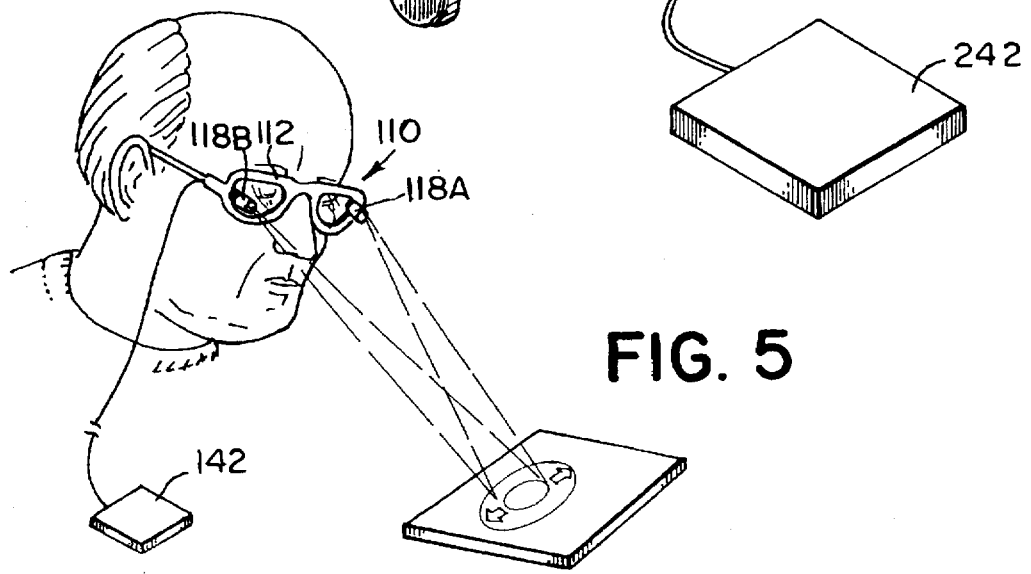
FIG. 5 is a perspective view which illustrates the operation of the first embodiment of the present invention to illustrate the feature of focusing the light emitted from the light source.

Referring now to FIG. 5, in use of the first embodiment 10, the light source 20 emits a light beam which is projected from the focusable light assembly 18A, 18B onto an object being viewed by the user. By adjusting the focusable light assemblies 18A, 18B relative to the frame 12, a user of the present invention can direct the light beam from each light source 20 to various angular positions relative to the users head. The user can move focusing sleeve 32 relative to base member 24 and thereby vary the distance between first lens 30 and second lens 34. As is well known by those skilled in the art, the change in the relative position of the two lenses changes the vergence of a beam of light passing through the two lenses 30, 34. A change in the vergence of the light beam can either increase or decrease the area of the illumination on the object to which the light beam is incident, with a corresponding decrease or increase, respectively, in the intensity of the illumination. Still with reference to FIG. 5, as the first preferred embodiment of the present invention has two focusable light assemblies 18A, 18B, the user can place both beams of light from light sources 20A, 20B on the same object, which would increase either the area or the intensity of the illumination, depending on the extent of the overlap of the beams, or the user could direct the light beams to different objects.

The use of the second preferred embodiment 110 is identical to the use of the first preferred embodiment 10 as discussed above.

The third preferred embodiment 210 is operated in a manner similar to the first preferred embodiment 10, as outlined above, with the following differences. As only one focusable light assembly 218 is included in the third preferred embodiment, the user directs the single beam of light upon one or more objects and moves the focusing sleeve 232 relative to the base member 224 to focus the light beam.

A principal advantage of the illumination device 10 of the present invention is its potential to improve the vision of persons suffering from macular degeneration. By enabling light to be focused on a particular object in a functioning area of a person's view field, the intensity of the illumination on that particular object can be increased. The increase in the intensity of illumination in the functioning view field area improves the visual perception of that area by an individual with macular degeneration, allowing such persons to have improved visual function in comparison to normal, unfocused illumination. The present invention is also of assistance to persons with various ether eye disorders, including cataracts. Furthermore, the feature of adjusting the intensity of the illumination makes the illumination devices 10, 110, 210 of the present invention particularly suitable for the use of persons performing detail work, such as repairing electronic devices or creating needlepoint artwork. Another advantage of the present invention is its ability to direct the emitted light beams over a wide area without the user having to adjust his or her head position of the their head due to the pivotal mounting of the light assemblies 18 to the frame 12 with ball and socket joints 26.

It will be appreciated by those skilled in the art that changes could be made to the embodiments described above without departing from the broad inventive concepts thereof. It is understood, therefore, that this invention is not limited to the particular embodiments disclosed, but it is intended to cover modifications within the spirit and scope of the present invention as defined by the appended claims.

I claim:

1. An illumination device for mounting on the head of a user, said device comprising:
 a frame having a cross member and a pair of rearwardly extending temple members attached to opposite ends of said cross member; and
 a focusable light assembly mounted on each end of said cross member by a pivotable connection, each focusable light assembly including a base member with a light source for emitting light and a first lens, and a focusing sleeve movably engaged with the base member and having a second lens mounted therein, said focusing sleeve being axially displaceable with respect to said base member by the user to vary the distance between said first lens and said second lens to at least one of converge and diverge the light emitted from said light source, each focusable light assembly being aimable by movement on the pivotable connection such that both light assemblies illuminate a selected area in a user's view field.

2. The illumination device as recited in claim 1, further including an electrical connector attached to said frame, said electrical connector being in electrical communication with each of said light sources and with a power source.

3. The illumination device as recited in claim 1, wherein said frame is usable with a pair of eyeglasses.

4. The illumination device as recited in claim 1, wherein said frame further includes a pair of lens sockets attached to said cross member and two lenses, each of said lenses being mounted within one of said lens sockets.

5. The illumination device as recited in claim 1, further including a battery compartment on said frame and at least one battery disposed within said battery compartment and being in electrical communication with at least one of said light sources.

6. The illumination device as recited in claim 1, wherein each of said base members of said two focusable light assemblies is rotatably mounted to said frame by a ball and socket joint.

7. An illumination device for mounting on the head of a user, said device comprising:
 a frame having a cross member and a pair of rearwardly extending temple members attached to opposite ends of said cross member;
 two focusable light assemblies rotatably mounted to said frame on opposite ends of said cross member, each of said focusable light assemblies including a base member mounted to said frame by a ball and socket joint, each base member having a cavity and a first lens mounted in said cavity, a light source disposed within said cavity of said base member for emitting light, and a focusing sleeve movably engaged with said base member and having a second lens mounted therein, said focusing sleeve being axially displaceable with respect to said base member by the user to vary the distance between said first lens and said second lens to at least one of converge and diverge the light emitted from said light source; and
 an electrical connector attached to said frame, said electrical connector being in electrical communication with said light sources and being adapted to be in electrical communication with a power source.

8. The illumination device as recited in claim 7, wherein said frame further includes a pair of lens sockets attached to a bottom surface of said cross member and two lenses, each of said lenses being mounted within one of said lens sockets.

9. The illumination device as recited in claim 7, wherein said frame is usable with a pair of eyeglasses.

10. The illumination device as recited in claim 7, further including a battery compartment on said frame and at least one battery disposed within said battery compartment and in electrical communication with at least one of said light sources and said electrical connector.

* * * * *